(12) United States Patent
Altman et al.

(10) Patent No.: US 6,902,932 B2
(45) Date of Patent: Jun. 7, 2005

(54) HELICALLY ORGANIZED SILK FIBROIN FIBER BUNDLES FOR MATRICES IN TISSUE ENGINEERING

(75) Inventors: Gregory H. Altman, Dedham, MA (US); David L. Kaplan, Concord, MA (US); Rebecca L. Horan, Westfield, MA (US); David J. Horan, Westfield, MA (US)

(73) Assignees: Tissue Regeneration, Inc., Medford, MA (US); Trustees of Tufts College, Medford, MA (US)

( * ) Notice: Subject to any disclaimer, the term of this patent is extended or adjusted under 35 U.S.C. 154(b) by 0 days.

(21) Appl. No.: 10/008,924

(22) Filed: Nov. 16, 2001

(65) Prior Publication Data

US 2003/0100108 A1 May 29, 2003

(51) Int. Cl.[7] ............................. C12N 5/06; C12N 5/08; C12N 11/08; C12N 11/04; A61F 2/00
(52) U.S. Cl. ..................... 435/395; 424/423; 424/93.7; 435/177; 435/180; 435/182
(58) Field of Search ................................ 435/174, 177, 435/180, 182, 395; 424/423, 93.7

(56) References Cited

U.S. PATENT DOCUMENTS

| | | | |
|---|---|---|---|
| 848,605 A | 3/1907 | Schmid | |
| 1,709,662 A | 4/1929 | Ellis | |
| 1,815,279 A | 7/1931 | Takamine, Jr. | |
| 1,828,736 A | 10/1931 | Harvey | |
| 1,896,494 A | 2/1933 | Myers et al. | |
| 1,927,022 A | 9/1933 | Bueno | 8/2 |
| 1,990,588 A | 2/1935 | Fink et al. | 18/54 |
| 2,040,949 A | 5/1936 | Olpin et al. | 8/2 |
| 4,141,207 A | 2/1979 | Mizushima et al. | 57/243 |
| 4,461,298 A * | 7/1984 | Shalaby et al. | 128/335.5 |
| 4,865,031 A | 9/1989 | O'Keefe | 128/334 R |
| 5,252,285 A | 10/1993 | Lock | 264/202 |
| 5,456,697 A | 10/1995 | Chesterfield et al. | 606/228 |
| 5,736,399 A * | 4/1998 | Takezawa et al. | 435/399 |
| 5,951,506 A | 9/1999 | Tsubouchi | 602/48 |
| 5,965,125 A | 10/1999 | Mineau-Hanschke | 424/93.21 |
| 5,994,099 A * | 11/1999 | Lewis et al. | 435/69.1 |
| 6,303,136 B1 * | 10/2001 | Li et al. | 424/424 |
| 6,440,740 B1 | 8/2002 | Tsubouchi et al. | 435/402 |
| 6,530,956 B1 * | 3/2003 | Mansmann | 623/18.11 |

FOREIGN PATENT DOCUMENTS

| | | |
|---|---|---|
| EP | 1 241 178 A1 | 9/2002 |
| WO | WO 02/29141 A1 | 4/2002 |

OTHER PUBLICATIONS

Gosline, et al., "The Mechanical Design of Spider Silks: from Fibroin Sequence to Mechanical Function", *The Journal of Experimental Biology*, 202:3295–3303 (1999).
Hinman, et al., "Synthetic Spider Silk: A Modular Fiber", *TIBTECH*, 18:374–379 (2000).
Yong–woo Lee, Silk Reeling and Testing Manual, FAO Agricultural Services Bulletin No. 136, Food and Agriculture Organization of the United Nations, Rome (1999), available at: http://www.fao.org/docrep/x2099e00.htm.
Xu, et al., Structure of a Protein Superfiber: Spider Dragline Silk, *Proc. Natl. Acad. Sci. USA*, 87:7120–7124 (1990).
Zhao, et al., "Structural Characterization and Artificial Fiber Formation of Bombyx mori Silk Fibroin in Hexafluoro–Iso–Propanol Solvent System", *Biopolymers*, 69:253–259 (2003).
Furuzono, T. et al., Biomaterials, 21:327–333 (2000).
Gotoh, Yohko et al., J. Biomed. Mater Res., 39:351–357 (1998).
Gotoh, Yohko et al., Biomaterials, 18:267–271 (1997).
Kurosaki, Sadayuki et al., J. Nippon Med. Sch., 66:41–44 (1999).
Liang, C.X. et al., Journal of Applied Polymer Science, 45:1937–43 (1992).
Minoura, Norihiko et al., Journal of Biomedical Materials Research, 29:1215–1221 (1995).
Minoura, Norihiko et al., Biomaterials, 11:430–434 (1990).
Santin, Matteo et al., J. Biomed. Mater Res., 46:382–89 (1999).
Hoechst Celanese, Dictionary of Fiber & Textile Technology, pp. 140–141 (1990).

* cited by examiner

*Primary Examiner*—David M. Naff
(74) *Attorney, Agent, or Firm*—Nixon Peabody LLP

(57) ABSTRACT

The present invention provides a novel silk-fiber-based matrix having a wire-rope geometry for use in producing a ligament or tendon, particularly an anterior cruciate ligament, ex vivo for implantation into a recipient in need thereof. The invention further provides the novel silk-fiber-based matrix which is seeded with pluripotent cells that proliferate and differentiate on the matrix to form a ligament or tendon ex vivo. Also disclosed is a bioengineered ligament comprising the silk-fiber-based matrix seeded with pluripotent cells that proliferate and differentiate on the matrix to form the ligament or tendon. A method for producing a ligament or tendon ex vivo comprising the novel silk-fiber-based matrix is also disclosed.

19 Claims, 8 Drawing Sheets

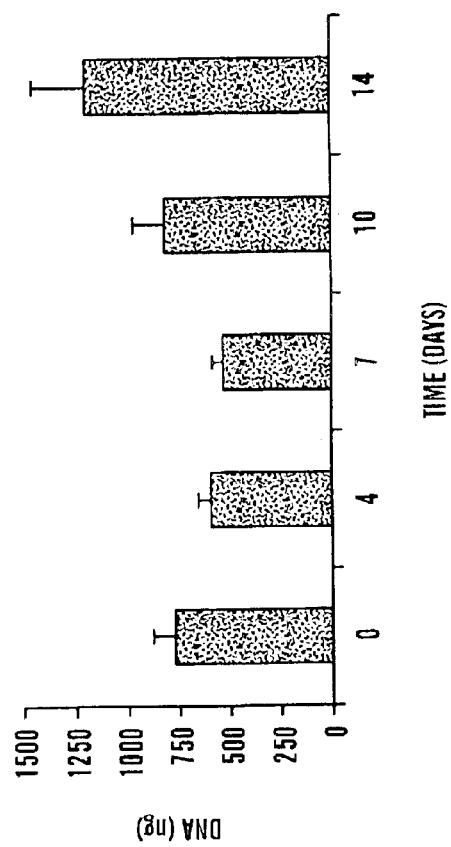
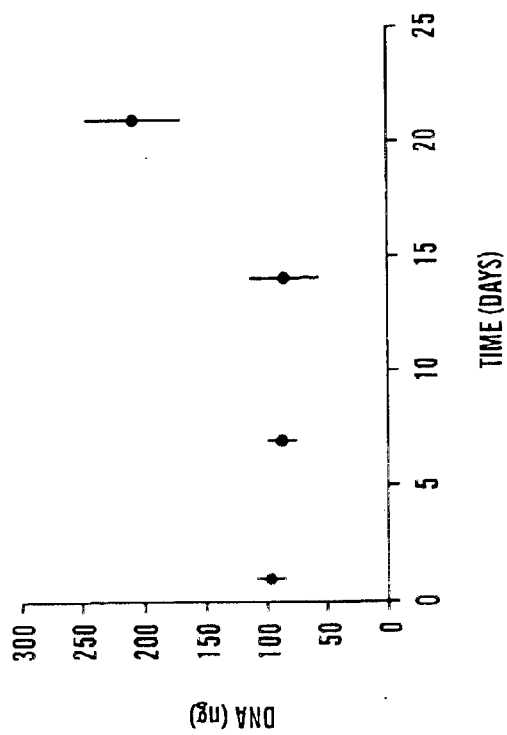
FIG. 6B
FIG. 6A

HELICALLY ORGANIZED SILK FIBROIN FIBER BUNDLES FOR MATRICES IN TISSUE ENGINEERING

GOVERNMENT RIGHTS

This invention was made with Government support under contract numbers DE13405 and AR46563 awarded by the National Institutes of Health and under contract number R43 HD42352 awarded by the National Institutes of Health through SBIR. The Government has certain rights in this invention.

FIELD OF THE INVENTION

The present invention is directed to a matrix or scaffold used in the production of bioengineered tissue, particularly ligaments and tendons. More particularly, the invention relates to a novel silk-fiber-based matrix upon which pluripotent cells may be seeded ex vivo and which proliferate and differentiate thereon into an anterior cruciate ligament for implantation into a recipient in need thereof.

BACKGROUND OF THE INVENTION

Every year, hundreds of thousands of Americans sprain, tear, or rupture ligaments and tendons of the knee, elbow, hand, shoulder, wrist and jaw (Langer et al., *Science* 260: 920–926 (1993)). Of particular importance is the anterior cruciate ligament of the knee. More than 200,000 people in the U.S. alone, will tear or rupture their anterior cruciate ligament (ACL) each year (Albright et al., 1999. Chapter 42-Knee and Leg:Soft-Tissue Trauma. In *Orthopaedic Knowledge Update* 6. American Academy of Orthopaedic Surgeons).). The ACL serves as a primary stabilizer of anterior tibial translation and as a secondary stabilizer of valgus-varus knee angulation, and is often susceptible to rupture or tear resulting from a flexion-rotation-valgus force associated with sports injuries and traffic accidents. Ruptures or tears often result in severe limitations in mobility, pain and discomfort, and the loss of an ability to participate in sports and exercise. Failures of the ACL are classified in three categories: (1) ligamentous (ligament fibers pull apart due to tensile stress), (2) failure at the bone-ligament interface without bone fracture, and (3) failure at the bone-ligament interface with bone fracture at the attachment site of bone and ligament. The most common type of ACL failure is the first category, ligamentous.

It is widely known throughout the medical community that the ACL has poor healing capabilities. Total surgical replacement and reconstruction are required when injury to the ACL involves significant tear or rupture. Four options have been utilized for repair or replacement of a damaged ACL: (1) autografts, (2) allografts, (3) xenografts, and (4) synthetic prostheses (degradable and non-degradable). To date, no surgical repair procedure has been shown to restore knee function completely, and novel treatment options would likely benefit a large number of patients.

The problems associated with the use of synthetic ACL replacements, along with the limited availability of the donor tissue, have motivated research towards the development of functional and biocompatible equivalents of native tissues. This shift from synthetic to biologically-based ACL replacements first applied in early studies in which collagenous ACL prostheses were prepared as composite structures consisting of reconstituted type I collagen fibers in a collagen I matrix with polymethylmethacrylate bone fixation plugs, and used as anterior cruciate ligament replacement tissues in rabbits (Dunn et al., *Am. J. Sports Medicine* 20: 507–515 (1992)). Subsequent studies incorporated active biological components into the process, such as ligament fibroblasts seeded on cross-linked collagen fiber scaffolds that were used as ligament analogs (Dunn et al., *J. Biomedical Materials Res.* 29: 1363–1371 (1995); Dunn, M. G., *Materials Res. Soc. Bulletin*, Nov: 43–46 (1996)), and suggested that structures approximating native ligaments can be generated.

A tendon gap model, based on pre-stressed collagen sutures seeded with mesenchymal stem cells provided improved repair of large tendon defects (Young et al., 1998). Goulet et al. modified the collagen-fibroblast system by using ligament fibroblasts in non-cross-linked collagen, with bone anchors to pre-stress the tissue and facilitate surgical implantation (Goulet et al., Tendons and Ligaments. In *Principles of Tissue Engineering*, Ed. R. Lanza, R. Langer, W. Chick. R. G. Landes Co. pp 633–643, R. G. Lanz Co. and Academic Press, Inc., San Diego, Calif. (1997)). Passive tension produced by growing the new ligament in a vertical position induced fibroblast elongation and the alignment of the cells and surrounding extracellular matrix.

Silk has been shown to offer new options for the design of biomaterials and tissue-engineering scaffolds with a wide range of mechanical properties (Sofia, S., et al., *J. Biol. Mat. Res.* 54: 139–148 (2001). For example, the dragline silk from the orb weaving spider, *Nephilia clavipes*, has the highest strength of any natural fiber, and rivals the mechanical properties of synthetic high performance fibers. Silks also resist failure in compression, are stable at high physiological temperatures, and are insoluble in aqueous and organic solvents. In recent years, silks have been studied as a model for the study of structure-function relationships of fibrous proteins. The manipulation of silk genes, both native and artificial versions, has provided insight into silk protein expression, assembly, and properties. Thus, biocompatibility, the ability to engineer the materials with specific and impressive mechanical properties, and a diverse range of surface chemistries for modification or decoration suggests that silk may provide an important class of biomaterial. Recent studies by the inventors of the present invention have demonstrated the successful attachment and growth of fibroblasts on silk films from silkworm silk of *Bombyx mori*.

Tissue engineering can potentially provide improved clinical options in orthopaedic medicine through the in vitro generation of biologically based functional tissues for transplantation at the time of injury or disease. Further, adult stem cells are becoming increasingly recognized for their potential to generate different cell types and thereby function effectively in vitro or in vivo in tissue repair. (Sussman, M. *Nature* 410: 640 (2001). The knee joint geometry and kinematics and the resultant effects on ACL structure must be incorporated into the construct design if a tissue engineered ACL generated in vivo is to successfully stabilize the knee and function in vivo. A mismatch in the ACL structure-function relationship would result in graft failure.

To date, no human clinical trials have been reported with tissue culture bioengineered anterior cruciate ligaments. This is due to the fact that each approach has failed to address one or more of the following issues: (1) the lack of a readily available cell or tissue source, (2) the unique structure (e.g., crimp pattern, peripheral helical pattern and isometric fiber organization) of an ACL, and (3) the necessary remodeling time in vivo for progenitor cells to differentiate and/or autologous cells to infiltrate the graft, thus extending the time a patient must incur a destabilized knee and rehabilitation. The development of a matrix for generating more fully functional bioengineered anterior cruciate ligaments would greatly benefit the specific field of knee reconstructive surgery, and would also provide wider benefits to the overall field of in vitro tissue generation and replacement surgery.

SUMMARY OF THE INVENTION

The present invention provides a novel silk-fiber-based matrix for producing ligaments and tendons ex vivo. More specifically, the present invention is directed to engineering mechanically and biologically functional anterior cruciate ligament using a novel silk-fiber-based matrix that may be seeded with pluripotent cells, such as bone marrow stromal cells (BMSCs). The mechanically and biologically autologous or allogenic anterior cruciate ligament comprised of the novel matrix and pluripotent cells may be prepared within a bioreactor environment to induce de novo ligament tissue formation in vitro prior to implantation. Surprisingly, it has now been found that the novel silk-fiber-based matrix supports BMSC differentiation towards ligament lineage without the need for directed mechanical stimulation during culture within a bioreactor. The inventors believe that mechanical stimulation will serve only to enhance the differentiation and tissue development process.

The present invention also provides a method for the generation of tissue engineered ACL ex vivo using the novel silk-fiber-based matrix that comprises the steps of seeding pluripotent stem cells in the silk-fiber-based matrix, anchoring the seeded matrix by attachment to at least two anchors, and culturing the cells within the matrix under conditions appropriate for cell growth and regeneration. The culturing step may comprise the additional step of subjecting the matrix to one or more mechanical forces via movement of one or both of the attached anchors. In a preferred embodiment for producing an ACL, pluripotent cells, and more particularly bone marrow stromal cells, are used. Suitable anchor materials comprise any materials to which the matrix can attach (either temporarily or permanently), and which supports ligament and tendon tissue growth or bone tissue growth at the anchors. Preferred anchor materials include hydroxyappatite, demineralized bone, and bone (allogenic or autologous). Anchor materials may also include titanium, stainless steel, high density polyethylene, Dacron and Teflon, amongst other materials. Goinopra coral which has been treated to convert the calcium carbonate to calcium phosphate has also been used as an anchor material. In a preferred embodiment, the mechanical forces to which the matrix may be subjected mimic mechanical stimuli experienced by an anterior cruciate ligament in vivo. This is accomplished by delivering the appropriate combination of tension, compression, torsion and shear, to the matrix.

The bioengineered ligament which is produced according to the present invention is advantageously characterized by a cellular orientation and/or matrix crimp pattern in the direction of applied mechanical forces, and also by the production of ligament and tendon specific markers including collagen type I, collagen type III, and fibronectin proteins along the axis of mechanical load produced by the mechanical forces or stimulation, if such forces are applied. In a preferred embodiment, the ligament or tendon is characterized by the presence of fiber bundles which are arranged into a helical organization.

Another aspect of the present invention is a method for producing a wide range of ligament and tendon types ex vivo using the novel silk-fiber-based matrix, and an adaptation of the method for producing an anterior cruciate ligament by adapting the matrix (e.g., geometry, organization, composition)(see Example 1) and anchor size to reflect the size of the specific type of ligament or tendon to be produced (e.g., posterior cruciate ligament, rotator cuff tendons, medial collateral ligament of the elbow and knee, flexor tendons of the hand, lateral ligaments of the ankle and tendons and ligaments of the jaw or temporomandibular joint), and also adapting the specific combination of forces applied, to mimic the mechanical stimuli experienced in vivo by the specific type of ligament or tendon to be produced. Similar adaptations of this method, and which are considered to be a part of the invention, can be made to produce other tissues ex vivo from pluripotent stem cells, by adapting additional matrix compositions, geometries, organizations, and the mechanical forces applied during cell culture to mimic stresses experienced in vivo by the specific tissue type to be produced. The methods of the present invention can be further modified to incorporate other stimuli experienced in vivo by the particular developing tissue. Some examples of other stimuli include chemical stimuli and electromagnetic stimuli.

As used herein, the term "tissue" is intended to take on its generally recognized biological/medical definition to those of skill in the art. As a non-limiting example, "tissue" is defined in Stedman's Medical Dictionary as:

[A] collection of similar cells and the intercellular substances surrounding them. There are four basic tissues in the body: 1) epithelium; 2) the connective tissues, including blood, bone, and cartilage; 3) muscle tissue; and 4) nerve tissue.

Another aspect of the present invention relates to the specific ligaments or tendons which are produced by the methods of the present invention. Some examples of ligaments or tendons that can be produced include anterior cruciate ligament, posterior cruciate ligament, rotator cuff tendons, medial collateral ligament of the elbow and knee, flexor tendons of the hand, lateral ligaments of the ankle and tendons and ligaments of the jaw or temporomandibular joint. Other tissues that may be produced by methods of the present invention include cartilage (both articular and meniscal), bone, muscle, skin and blood vessels.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

BRIEF DESCRIPTION OF THE FIGURES

FIG. 6A is a chart illustrating bone marrow stromal cell proliferation on silk fibroin Matrix 1 determined by total cellular DNA over 21 day culture period indicating a significant increase in cell proliferation after 21 days of culture;

FIG. 6B is a bar graph illustrating bone marrow stromal cell proliferation on silk fibroin Matrix 2 determined by total cellular DNA over 14 day culture period indicating a significant increase in cell proliferation after 14 days of culture;

DETAILED DESCRIPTION OF THE INVENTION

The present invention is directed to a novel silk-fiber-based matrix upon which pluripotent cells may be seeded and which proliferate and differentiate into ligament and tendon fibroblasts resulting in the formation of an anterior cruciate ligament (ACL), or other ligaments, tendons or tissues. The novel silk-fiber-based matrix is designed having fibers in a wire-rope (twisted or braided-like) geometry, which exhibits mechanical properties identical to a natural anterior cruciate ligament (see Table 1, infra) and where simple variations in matrix organization and geometry can result in the formation of any desired ligament or tendon tissue (see Table 2, infra).

The present invention is also based on the finding that pluripotent bone marrow stromal cells (BMSCs) isolated and cultured as described in Example 1, seeded on the is silk-fiber-based matrix, and cultured in a bioreactor under static conditions will undergo ligament and tendon specific differentiation forming viable tissue. In addition, the histo-morphological properties of a bioengineered tissue produced in vitro generated from pluripotent cells within a matrix are affected by the direct application of mechanical force to the matrix during tissue generation. This discovery provides important new insights into the relationship between mechanical stress, biochemical and cell immobilization methods and cell differentiation, and has applications in producing a wide variety of ligaments, tendons and tissues in vitro from pluripotent cells.

Figure 2A:
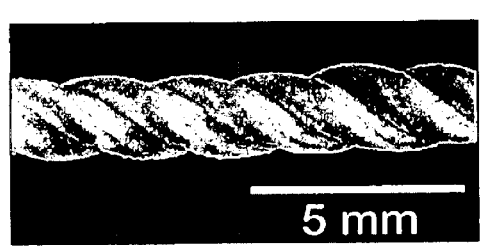
FIG. 2A illustrates a single cord of Matrix 1 having a wire-rope geometry composed of two levels of twisting hierarchy. When six cords are used in parallel (e.g., Matrix 1), the matrix has mechanical properties similar to a native ACL.
Figure 2B:
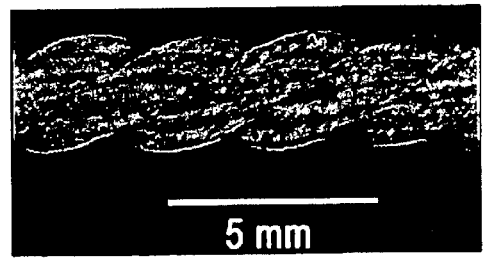
FIG. 2B illustrates a single cord of Matrix 2 having a wire-rope geometry composed of three levels of twisting hierarchy. When six cords are used in parallel (e.g., Matrix 2), the matrix has mechanical properties similar to a native ACL.

One aspect of the present invention relates to a matrix comprised of silk fibers having a wire-rope (twisted or braided-like) geometry, as illustrated in FIGS. 2A and 2B.

Figure 1A:
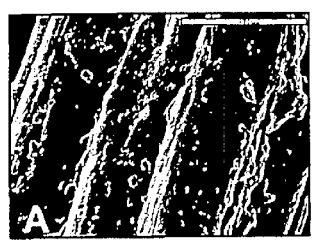
FIG. 1A is a scanning electron microscopy (SEM) image of single native silk fiber having a sericin coating.
Figure 1B:
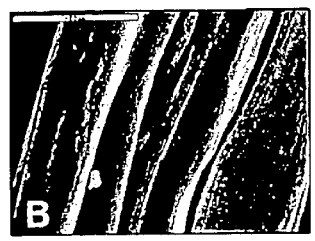
FIG. 1B illustrates SEM of the silk fiber of FIG. 1A extracted for 60 min at 37° C.
Figure 1C:
FIG. 1C illustrates SEM of the silk fiber of FIG. 1A extracted for 60 min at 90° C. and illustrating complete removal of the sericin coating.

As described in the Examples below, mechanical properties of the silk fibroin (as illustrated in FIGS. 1A–C) were characterized and geometries for forming applicable matrices for ACL engineering were derived using a theoretical computational model (see FIG. 1D). A six-cord construct was chosen for use as an ACL replacement to increase matrix surface area and to enhance support for tissue in-growth. Two of several optimal construct geometrical hierarchies have been determined to comprise the following: Matrix 1: 1 ACL prosthesis=6 parallel cords; 1 cord=3 twisted strands (3 twists/cm); 1 strand=6 twisted bundles (3 twists/cm); 1 bundle=30 parallel washed fibers; and Matrix 2: 1 ACL matrix=6 parallel cords; 1 cord=3 twisted strands (2 twists/cm); 1 strand=3 twisted bundles (2.5 twists/cm); 1 bundle=3 groups (3 twists/cm); 1 group=15 parallel extracted silk fibroin fibers. The number of fibers and geometries for Matrix 1 and Matrix 2 were selected such that the silk prostheses are similar to the ACL biomechanical properties in ultimate tensile strength, linear stiffness, yield point and % elongation at break, serving as a solid starting point for the development of a tissue engineered ACL. The ability to generate two matrices with differing geometries both resulting in mechanical properties which mimic properties of the ACL indicates that an infinite number of geometrical configurations exist to achieve the desired mechanical properties. One skilled in the art will recognize that an alternative geometry for any desired ligament or tendon tissue may comprise any number, combination or organization of cords, strands, bundles, groups and fibers (see Table 2, infra) that result in a matrix is construct with applicable mechanical properties that mimic those of the ligament or tendon desired. For example, one (1) ACL prosthesis may have any number of cords in parallel ranging from a single cord to an infinite number of cords provided there is a means of anchoring the final matrix in vitro or in vivo. One skilled in the art would also recognize that no limit exists to the number of twisting levels (where a single level is defined as either a group, bundle, strand or cord) for a given geometry providing the matrix results in the desired mechanical properties. Furthermore, one skilled in the art would realize the large degree of freedom in designing the matrix geometry and organization in engineering an ACL prosthesis, and will therefore understand the utility of the developed theoretical computational model to predict the matrix design of a desired ligament or tendon tissue (see Example 1). One skilled in the art would, therefore, recognize that a variation in geometry (i.e., the number of cords used to make a prosthesis or number of fibers in a group) could be used to generate matrices applicable to most ligaments and tendons. For example, for smaller ligaments or tendons of the hand, the geometry and organization used to generate a single cord of Matrix 1 (or two cords or three cords, etc.) may be appropriate given the matrix's organization results in mechanical properties suitable for the particular physiological environment.

The invention is not, however, limited with respect to the wire-rope geometry as described, and any geometry or combinations of geometries (e.g., parallel, twisted, braided, mesh-like) can be used that results in matrix mechanical properties similar to the ACL (i.e., >2000 N ultimate tensile strength, between 100–600 N/mm linear stiffness for a native ACL or commonly used replacement graft such as the patellar tendon with length between 26–30 mm) or to the desired ligament and tendon that is to be produced. The number of fibers and geometry of both Matrix 1 and Matrix 2 were selected to generate mechanically appropriate ACL matrices, or other desired ligament or tendon matrices (e.g., posterior cruciate ligament (PCL)). For example, a single cord of the six-cord Matrix 1 construct was used to reconstruct the medial collateral ligament (MC) in a rabbit (see FIG. 9). The mechanical properties of the silk six-cord constructs of Matrix 1 and Matrix 2 are described in Table 1 and in FIG. 3. Additional geometries and their relating mechanical properties are listed in Table 2 as an example of the large degree of design freedom that would result in a matrix applicable in ACL tissue engineering in accordance with the present invention.

TABLE 1

|  | UTS (N) | Stiffness (N/mm) | Yield Pt. (N) | Elongation (%) |
|---|---|---|---|---|
| Silk matrix 1 | 2337 +/− 72 | 354 +/− 26 | 1262 +/− 36 | 38.6 +/− 2.4 |
| Silk Matrix 2 | 3407 +/− 63 | 580 +/− 40 | 1647 +/− 214 | 29 +/− 4 |
| Human ACL | 2160 +/− 157[4] | 242 +/− 28[4] | ~1200 | ~26–32% |

Mechanical properties for two different cords based on a cord length of 3 cm.

TABLE 2

| Twisting Level (# of twists/cm) | Matrix 1 | Matrix 2 | Matrix 3 | Matrix 4 | Matrix 5 | Matrix 6 | Matrix 7 |
|---|---|---|---|---|---|---|---|
| # fibers per group | 30 (0) | 15 (0) | 1300 (0) | 180 (0) | 20 (0) | 10 (0) | 15 (0) |
| # groups per bundle | 6 (3) | 3 (3) | 3 (2) | 3 (3.5) | 6 (3) | 6 (3) | 3 (3) |
| # bundles per strand | 3 (3) | 6 (2.5) | 1 (0) | 3 (2) | 3 (2) | 3 (2.5) | 3 (2.5) |
| # strands per cord | 6 (0) | 3 (2.0) | — | 2 (0) | 3 (1) | 3 (2) | 3 (2) |
| # cords per ACL | — | 6 (0) | — | — | 3 (0) | 6 (0) | 12 (0) |
| UTS (N) | 2337 | 3407 | 2780 | 2300 | 2500 | 2300 | 3400 |
| Stiffness (N/mm) | 354 | 580 | 300 | 350 | 550 | 500 | 550 |

Examples of several geometry hierarchies that would result in suitable mechanical properties for replacement of the ACL.
Note:
Matrix 1 and 2 have been developed as shown in example 1;
Matrix 3 would yield a single bundle prosthesis,
Matrix 4 would yield a 2 strand prosthesis,
Matrix 5 would yield a 3 cord prosthesis,
Matrix 6 is another variation of a 6 cord prosthesis, and
Matrix 7 will yield a 12 cord prosthesis.

Advantageously, the silk-fiber based matrix is comprised solely of silk. Types and sources of silk include the following: silks from silkworms, such as *Bombyx mori* and related species; silks from spiders, such as *Nephila clavipes*; silks from genetically engineered bacteria, yeast mammalian cells, insect cells, and transgenic plants and animals; silks obtained from cultured cells from silkworms or spiders; native silks; cloned full or partial sequences of native silks; and silks obtained from synthetic genes encoding silk or silk-like sequences. In their raw form, the native silk fibroin obtained from the *Bombyx mori* silkworms are coated with a glue-like protein called sericin, which typically is extracted from the fibers before the fibers which make up the matrix are seeded with cells.

In an alternative embodiment, the matrix may be comprised of a composite of: (1) silk and collagen fibers (2) silk and collagen foams, meshes, or sponges, or a composite of (3) silk fibroin fibers and silk foams, meshes, or sponges, (4) silk and biodegradable polymers (e.g., cellulose, cotton, gelatin, poly lactide, poly glycolic, poly(lactide-co-glycolide), poly caproloactone, polyamides, polyanhydrides, polyaminoacids, polyortho esters, poly acetals, proteins, degradable polyurethanes, polysaccharides, polycyanoacrylates, Glycosamino glycans—e.g., chrondroitin sulfate, heparin, etc., Polysaccharides—native, reprocessed or genetically engineered versions—e.g. hyaluronic acid, alginates, xanthans, pectin, chitosan, chitin, and the like., Elastin—native, reprocessed or genetically engineered and chemical versions, Collagens—native, reprocessed or genetically engineered versions), or (5) silk and non-biodegradable polymers (e.g., polyamide, polyester, polystyrene, polypropylene, polyacrylate, polyvinyl, polycarbonate, polytetrafluorethylene, or nitrocellulose material. The composite generally enhances the matrix properties such as porosity, degradability, and also enhances cell seeding, proliferation, differentiation or tissue development. FIG. 10 illustrates the ability of collagen fibers to support BMSC growth and ligament specific differentiation.

The matrix of the present invention may also be treated to enhance cell proliferation and/or tissue differentiation thereon. Exemplary matrix treatments for enhancing cell proliferation and tissue differentiation include, but are not limited to, metals, irradiation, crosslinking, chemical surface modifications (e.g. RGD (arg-gly-asp) peptide coating, fibronectin coating, coupling growth factors), and physical surface modifications.

A second aspect of the present invention relates to a mechanically and biologically functional ACL formed from a novel silk-fiber-based matrix and autologous or allogenic (depending on the recipient of the tissue) bone marrow stromal cells (BMSCs) seeded on the matrix. The silk-fiber-based matrix induces stromal cell differentiation towards ligament lineage without the need for any mechanical stimulation during bioreactor cultivation. BMSCs seeded on the silk-fiber-based matrix and grown in a petri dish begin to attach and spread (see FIG. 4), proliferate covering the matrix (see FIGS. 5 and 6) and differentiate as shown by the expression of ligament specific markers (see FIG. 8). Markers for cartilage (collagen type II) and for bone (bone sialoprotein) were not expressed (see FIG. 8). Data illustrating the expression of ligament specific markers is set forth in Example 2.

In another aspect, the present invention relates to a method for producing an ACL ex vivo. Cells capable of differentiating into ligament cells are grown under conditions which simulate the movements and forces experienced by an ACL in vivo through the course of embryonic development into mature ligament function. This is accomplished by the following steps: under sterile conditions, pluripotent cells are seeded within a three dimensional silk-fiber-based matrix to which cells can adhere and which is advantageously of cylindrical shape. The three dimensional silk-fiber based matrix used in the method serves as a preliminary matrix, which is supplemented and possibly even replaced by extracellular matrix components produced by the differentiating cells. Use of the novel silk-fiber-based matrix may enhance or accelerate the development of the ACL.

For instance, the novel silk-fiber-based matrix which has specific mechanical properties (e.g., increased tensile strength) that can withstand strong forces prior to reinforcement from cellular extracellular matrix components. Other advantageous properties of the novel silk-fiber based preliminary matrix include, without limitation, biocompatibility and susceptibility to biodegradation.

The pluripotent cells may be seeded within the preliminary matrix either pre- or post-matrix formation, depending upon the particular matrix used and the method of matrix formation. Uniform seeding is preferable. In theory, the number of cells seeded does not limit the final ligament produced, however optimal seeding may increase the rate of generation. Optimal seeding amounts will depend on the specific culture conditions. In one embodiment, the matrix is seeded with from about 0.05 to 5 times the physiological cell density of a native ligament.

One or more types of pluripotent cells are used in the method. Such cells have the ability to differentiate into a wide variety of cell types in response to the proper differentiation signals and to express ligament specific markers. More specifically, the method requires the use of cells that have the ability to differentiate into cells of ligament and tendon tissue. In a preferred embodiment, bone marrow stromal cells are used. If the resulting bioengineered ligament is to be transplanted into a patient, the cells should be derived from a source that is compatible with the intended recipient. Although the recipient will generally be a human, applications in veterinary medicine also exist. In one embodiment, the cells are obtained from the recipient (autologous), although compatible donor cells may also be used to make allogenic ligaments. For example, when making allogenic ligaments (e.g., using cells from another human such as bone marrow stromal cells isolated from donated bone marrow or ACL fibroblasts isolated from donated ACL tissue), human anterior cruciate ligament fibroblast cells isolated from intact donor ACL tissue (e.g. cadaveric or from total knee transplantations), ruptured ACL tissue (e.g., harvested at the time of surgery from a patient undergoing ACL reconstruction) or bone marrow stromal cells may be used. The determination of compatibility is within the means of the skilled practitioner.

In alternative embodiments of the present invention, ligaments or tendons including, but not limited to, the posterior cruciate ligament, rotator cuff tendons, medial collateral ligament of the elbow and knee, flexor tendons of the hand, lateral ligaments of the ankle and tendons and ligaments of the jaw or temporomandibular joint other than ACL, cartilage, bone and other tissues may be engineered with the matrix in accordance with the method of the present invention. In this manner, the cells to be seeded on the matrix are selected in accordance with the tissue to be produced (e.g., pluripotent or of the desired tissue type). Cells seeded on the matrix in accordance with the present invention may be autologous or allogenic. The use of autologous cells effectively creates an allograft or autograft for implantation in a recipient.

As recited, to form an ACL, cells, which are advantageously bone marrow stromal cells, are seeded on the matrix. Bone marrow stromal cells are a type of pluripotent cell, and are also referred to in the art as mesenchymal stem cells or simply as stromal cells. As recited, the source of these cells can be autologous or allogenic. The present invention also contemplates the use of adult or embryonic stem or pluripotent cells, in so long as the proper environment (either in vivo or in vitro), seeded on the silk-fiber based matrix, can recapitulate an ACL or any other desired ligament or tissue in extracellular matrix composition (e.g., protein, glycoprotein content) organization, structure or function.

Fibroblast cells are also contemplated by the present invention for seeding on the inventive matrix. Since fibroblast cells are often not referred to as pluripotent cells, fibroblasts are intended to include mature human ACL fibroblasts (autologous or allogenic) isolated from ACL tissue, fibroblasts from other ligament tissue, fibroblasts from tendon tissue, from netonatal foreskin, from umbilical cord blood, or from any cell, whether mature or pluripotent, mature dedifferentiated, or genetically engineered, such that when cultured in the proper environment (either in vivo or in vitro), and seeded on the silk-fiber based matrix, can recapitulate an ACL or any other desired ligament or tissue in extracellular matrix composition (e.g., protein, glycoprotein content), organization, structure or function.

The faces of the matrix cylinder are each attached to anchors, through which a range of forces are to be applied to the matrix. To facilitate force delivery to the matrix, it is preferable that the entire surface of each respective face of the matrix contact the face of the respective anchors. Anchors with a shape which reflects the site of attachment (e.g., cylindrical) are best suited for use in this method. Once assembled, the cells in the anchored matrix are cultured under conditions appropriate for cell growth and regeneration. The matrix is subjected to one or more mechanical forces applied through the attached anchors (e.g., via movement of one or both of the attached anchors) during the course of culture. The mechanical forces are applied over the period of culture to mimic conditions experienced by the native ACL, or other tissues in vivo.

The anchors must be made of a material suitable for matrix attachment, and the resulting attachment should be strong enough to endure the stress of the mechanical forces applied. In addition, it is preferable that the anchors be of a material which is suitable for the attachment of extracellular matrix which is produced by the differentiating cells. The anchors support bony tissue in-growth (either in vitro or in vivo) while anchoring the developing ligament. Some examples of suitable anchor material include, without limitation, hydroxyappatite, *Goinopra* coral, demineralized bone, bone (allogenic or autologous). Anchor materials may also include titanium, stainless steel, high density polyethylene, Dacron and Teflon.

Alternatively, anchor material may be created or further enhanced by infusing a selected material with a factor which promotes either ligament matrix binding or bone matrix binding or both. The term infuse is considered to include any method of application which appropriately distributes the factor onto the anchor (e.g., coating, permeating, contacting). Examples of such factors include without limitation, laminin, fibronectin, any extracellular matrix protein that promotes adhesion, silk, factors which contain arginine-glycine-aspartate (RGD) peptide binding regions or the RGD peptides themselves. Growth factors or bone morphogenic protein can also be used to enhance anchor attachment. In addition, anchors may be pre-seeded with cells (e.g., stem cells, ligament cells, osteoblasts, osteogenic progenitor cells) which adhere to the anchors and bind the matrix, to produce enhanced matrix attachment both in vitro and in vivo.

An exemplary anchor system is disclosed in applicant's co-pending application U.S. Ser. No. 09/950,561, filed Sep. 10, 2001 and currently pending. The matrix is attached to the anchors via contact with the anchor face or alternatively by actual penetration of the matrix material through the anchor material. Because the force applied to the matrix via the anchors dictates the final ligament produced, the size of the final ligament produced is, in part, dictated by the size of the attachment site of the anchor. One of skill in the art will appreciate that an anchor of appropriate size to the desired final ligament should be used. A preferred anchor shape for the formation of an ACL is a cylinder. However, one of skill in the art will appreciate that other anchor shapes and sizes will also function adequately. In a preferred embodiment, anchors have an appropriate size and composition for direct insertion into bone tunnels in the femur and tibia of a recipient of the bioengineered ligament.

In an alternative embodiment of the present invention, anchors may be used only temporarily during in vitro culture, and then removed when the matrix alone is implanted in vivo.

In another embodiment, the novel silk-fiber-based matrix is seeded with BMSCs and cultured in a bioreactor. Two types of growth environments currently exist that may be used in accordance with this invention: (1) the in vitro bioreactor apparatus system, and (2) the in vivo knee joint, which serves as a "bioreactor" as it provides the physiologic environment including progenitor cells and stimuli (both chemical and physical) necessary for the development of a viable ACL given a matrix with proper biocompatible and mechanical properties. The bioreactor apparatus provides optimal culture conditions for the formation of a ligament in terms of differentiation and extracellular matrix (ECM) production, and which thus provides the ligament with optimal mechanical and biological properties prior to implantation in a recipient. Additionally, when the silk-fiber based matrix is seeded and cultured with cells in vitro, a petri dish may be considered to be the bioreactor within which conditions appropriate for cell growth and regeneration exist, i.e., a static environment.

In accordance with the one embodiment of present invention, cells may also be cultured on the matrix without the application of any mechanical forces, i.e., in a static environment. For example, the silk-fiber based matrix alone, with no in vitro applied mechanical forces or stimulation, when seeded and cultured with BMSCs, induces the cells to proliferate and express ligament and tendon specific markers (See Example 2 and FIG. 8). The knee joint may serve as a physiological growth and development environment that can provide the cells and the correct environmental signals (chemical and physical) to the matrix such that an ACL technically develops. Therefore, the knee joint (as its own form of bioreactor) plus the matrix (either non-seeded, seeded and not differentiated in vitro, or seeded and differentiated in vitro prior to implantation) will result in the development of an ACL, or other desired tissue depending upon the cell type seeded on the matrix and the anatomical location of matrix implantation. FIG. 9 illustrates the effects of the medial collateral knee joint environment on medial collateral ligament (MCL) development when only a non-seeded silk-based matrix with appropriate MCL mechanical properties is implanted for 6 weeks in vivo. Whether the cells are cultured in a static environment with no mechanical stimulation applied, or in a dynamic environment, such as in a bioreactor apparatus, conditions appropriate for cell growth and regeneration are advantageously present for the engineering of the desired ligament or tissue.

In the experiments described in the Examples section below, the applied mechanical stimulation was shown to influence the morphology, and cellular organization of the progenitor cells within the resulting tissue. The extracellular matrix components secreted by the cells and organization of the extracellular matrix throughout the tissue was also significantly influenced by the forces applied to the matrix during tissue generation. During in vitro tissue generation, the cells and extracellular matrix aligned along the axis of load, reflecting the in vivo organization of a native ACL which is also along the various load axes produced from natural knee joint movement and function. These results suggest that the physical stimuli experienced in nature by cells of developing tissue, such as the ACL, play a significant role in progenitor cell differentiation and tissue formation. They further indicate that this role can be effectively duplicated in vitro by mechanical manipulation to produce a similar tissue. The more closely the forces produced by mechanical manipulation resemble the forces experienced by an ACL in vivo, the more closely the resultant tissue will resemble a native ACL.

When mechanical stimulation is applied in vitro to the matrix via a bioreactor, there exists independent but concurrent control over both cyclic and rotation strains as applied to one anchor with respect to the other anchor. In an alternative embodiment, the matrix alone may be implanted in vivo, seeded with ACL cells from the patient and exposed in vivo to mechanical signaling via the patient.

When the matrix is seeded with cells prior to implantation, the cells are cultured within the matrix under conditions appropriate for cell growth and differentiation. During the culture process, the matrix may be subjected to one or more mechanical forces via movement of one or both of the attached anchors. The mechanical forces of tension, compression, torsion and shear, and combinations thereof, are applied in the appropriate combinations, magnitudes, and frequencies to mimic the mechanical stimuli experienced by an ACL in vivo.

Various factors will influence the amount of force which can be tolerated by the matrix (e.g., matrix composition, cell density). Matrix strength is expected to change through the course of tissue development. Therefore, mechanical forces or strains applied will increase, decrease or remain constant in magnitude, duration, frequency and variety over the period of ligament generation, to appropriately correspond to matrix strength at the time of application.

When producing an ACL, the more accurate the intensity and combination of stimuli applied to the matrix during tissue development, the more the resulting ligament will resemble a native ACL. Two issues must be considered regarding the natural function of the ACL when devising the in vitro mechanical force regimen that closely mimics the in vivo environment: (1) the different types of motion experienced by the ACL and the responses of the ACL to knee joint movements and (2) the extent of the mechanical stresses experienced by the ligament. Specific combinations of mechanical stimuli are generated from the natural motions of the knee structure and transmitted to the native ACL.

To briefly describe the motions of the knee, the connection of the tibia and femur by the ACL between provides six degrees of freedom when considering the motions of the two bones relative to each other: the tibia can move in the three directions and can rotate relative to the axes for each of these three directions. The knee is restricted from achieving the full ranges of these six degrees of freedom due to the presence of ligaments and capular fibers and the knee surfaces themselves (Biden et al., Experimental methods used to evaluate knee ligament function. In *Knee Ligaments: Structure, Function, Injury and Repair*, Ed. D. Daniel et al. Raven Press, pp. 135–151(1990)). Small translational movements are also possible. The attachment sites of the ACL are responsible for its stabilizing roles in the knee joint. The ACL functions as a primary stabilizer of anterior-tibial translation, and as a secondary stabilizer of valgus-varus angulation, and tibial rotation (Shoemaker et al., The limits of knee motion. In *Knee Ligaments: Structure, Function, Injury and Repair*, Ed. D. Daniel et al. Raven Press, pp. 1534–161(1990)). Therefore, the ACL is responsible for stabilizing the knee in three of the six possible degrees of freedom. As a result, the ACL has developed a specific fiber organization and overall structure to perform these stabilizing functions. The present invention simulates these conditions in vitro to produce a tissue with similar structure and fiber organization.

The extent of mechanical stresses experienced by the ACL can be similarly summarized. The ACL undergoes cyclic loads of about 400 N between one and two million cycles per year (Chen et al., *J. Biomed. Mat. Res.* 14: 567–586 (1980). It is also critical to consider linear stiffness (~182 N/mm), ultimate deformation (100% of ACL) and energy absorbed at failure (12.8 N-m) (Woo et al., The tensile properties of human anterior cruciate ligament (ACL) and ACL graft tissues. In *Knee Ligaments: Structure, Function, Injury and Repair*, Ed. D. Daniel et al. Raven Press, pp. 279–289 (1990)) when developing an ACL surgical replacement.

The Examples section below details the production of a prototype bioengineered anterior cruciate ligament (ACL) ex vivo. Mechanical forces mimicking a subset of the mechanical stimuli experienced by a native ACL in vivo (rotational deformation and linear deformation) were applied in combination, and the resulting ligament which was formed was studied to determine the effects of the applied forces on tissue development. Exposure of the developing ligament to physiological loading during in vitro formation induced the cells to adopt a defined orientation along the axes of load, and to generate extracellular matrices along the axes as well. These results indicate that the incorporation of complex multi-dimensional mechanical forces into the regime to produce a more complex network of load axes that mimics the environment of the native ACL, will produce a bioengineered ligament which more closely resembles a native ACL.

The different mechanical forces that may be applied include, without limitation, tension, compression, torsion, and shear. These forces are applied in combinations which simulate forces experienced by an ACL in the course of natural knee joint movements and function. These movements include, without limitation, knee joint extension and flexion as defined in the coronal and sagittal planes, and knee joint flexion. Optimally, the combination of forces applied mimics the mechanical stimuli experienced by an anterior cruciate ligament in vivo as accurately as is experimentally possible. Varying the specific regimen of force application through the course of ligament generation is expected to influence the rate and outcome of tissue development, with optimal conditions to be determined empirically. Potential variables in the regimen include, without limitation: (1) strain rate, (2) percent strain, (3) type of strain, e.g. translation and rotation, (4) frequency, (5) number of cycles within a given regime, (6) number of different regimes, (7) duration at extreme points of ligament deformation, (8) force levels, and (9) different force combinations. It will be recognized by one of skill in the art that a potentially unlimited number of variations exist. In a preferred embodiment the regimen of mechanical forces applied produces helically organized fibers similar to those of the native ligament, described below.

The fiber bundles of a native ligament are arranged into a helical organization.

The mode of attachment and the need for the knee joint to rotate ~140° of flexion has resulted in the native ACL inheriting a 90° twist and with the peripheral fiber bundles developing a helical organization. This unique biomechanical feature allows the ACL to sustain extremely high loading. In the functional ACL, this helical organization of fibers allows anterior-posterior and posterior-anterior fibers to remain relatively isometric in respect to one another for all degrees of flexion, thus load can be equally distributed to all fiber bundles at any degree of knee joint flexion stabilizing the knee throughout all ranges of joint motion. In a preferred embodiment of the invention, mechanical forces that simulate a combination of knee joint flexion and knee joint extension are applied to the developing ligament to produce an engineered ACL which possesses this same helical organization. The mechanical apparatus used in the experiments presented in the Examples below provides control over strain and strain rates (both translational and rotational). The mechanical apparatus will monitor the actual load experienced by the growing ligaments, serving to 'teach' the ligaments over time through monitoring and increasing the loading regimes.

Another aspect of the present invention relates to the bioengineered anterior cruciate ligament produced by the above described methods. The bioengineered ligament produced by these methods is characterized by cellular orientation and/or a matrix crimp pattern in the direction of the mechanical forces applied during generation. The ligament is also characterized by the production/presence of extracellular matrix components (e.g., collagen type I, and type III, fibronectin, and tenascin-C proteins) along the axis of mechanical load experienced during culture. In a preferred embodiment, the ligament fiber bundles are arranged into a helical organization, as discussed above.

The above methods using the novel silk-fiber-based matrix are not limited to the production of an ACL, but can also be used to produce other ligaments and tendons found in the knee (e.g., posterior cruciate ligament) or other parts of the body (e.g., hand, wrist, ankle, elbow, jaw and shoulder), such as for example, but not limited to posterior cruciate ligament, rotator cuff tendons, medial collateral ligament of the elbow and knee, flexor tendons of the hand, lateral ligaments of the ankle and tendons and ligaments of the jaw or temporomandibular joint. All moveable joints in a human body have specialized ligaments which connect the articular extremities of the bones in the joint. Each ligament in the body has a specific structure and organization which is dictated by its function and environment. The various ligaments of the body, their locations and functions are listed in *Anatomy, Descriptive and Surgical* (Gray, H., Eds. Pick, T. P., Howden, R., Bounty Books, New York (1977)), the pertinent contents of which are incorporated herein by reference. By determining the physical stimuli experienced by a given ligament or tendon, and incorporating forces which mimic these stimuli, the above described method for producing an ACL ex vivo can be adapted to produce bioengineered ligaments and tendons ex vivo which simulates any ligament or tendon in the body.

The specific type of ligament or tendon to be produced is predetermined prior to tissue generation since several aspects of the method vary with the specific conditions experienced in vivo by the native ligament or tendon. The mechanical forces to which the developing ligament or tendon is subjected during cell culture are determined for the particular ligament or tendon type being cultivated. The specific conditions can be determined by those skilled in the art by studying the native ligament or tendon and its environment and function. One or more mechanical forces experienced by the ligament or tendon in vivo are applied to the matrix during culture of the cells in the matrix. The skilled practitioner will recognize that a ligament or tendon which is superior to those currently available can be produced by the application of a subset of forces experienced by the native ligament or tendon. However, optimally, the full range of in vivo forces will be applied to the matrix in the appropriate magnitudes and combinations to produce a final product which most closely resembles the native ligament or tendon. These forces include, without limitation, the forces described above for the production of an ACL. Because the mechanical forces applied vary with ligament or tendon type, and the final size of the ligament or tendon will be influenced by the anchors used, optimal anchor composition, size and matrix attachment sites are to be determined for each type of ligament or tendon by the skilled practitioner. The type of cells seeded on the matrix is obviously determined based on the type of ligament or tendon to be produced.

Another aspect of the present invention relates to the production of other tissue types ex vivo using methods similar to those described above for the generation of ligaments or tendons ex vivo. The above described methods can also be applied to produce a range of engineered tissue products which involve mechanical deformation as a major part of their function, such as muscle (e.g., smooth muscle, skeletal muscle, cardiac muscle), bone, cartilage, vertebral discs, and some types of blood vessels. Bone marrow stomal cells possess the ability to differentiate into these as well as other tissues. The geometry of the silk-based matrix or composite matrix can easily be adapted to the correct anatomical geometrical configuration of the desired tissue type. For example, silk fibroin fibers can be reformed in a cylindrical tube to recreate arteries.

The results presented in the Examples below indicate that growth in an environment which mimics the specific mechanical environment of a given tissue type will induce the appropriate cell differentiation to produce a bioengineered tissue which significantly resembles native tissue. The ranges and types of mechanical deformation of the matrix can be extended to produce a wide range of tissue structural organization. Preferably, the cell culture environment reflects the in vivo environment experienced by the native tissue and the cells it contains, throughout the course of embryonic development to mature function of the cells within the native tissue, as accurately as possible. Factors to consider when designing specific culture conditions to produce a given tissue include, without limitation, the matrix composition, the method of cell immobilization, the anchoring method of the matrix or tissue, the specific forces applied, and the cell culture medium. The specific regimen of mechanical stimulation depends upon the tissue type to be produced, and is established by varying the application of mechanical forces (e.g., tension only, torsion only, combination of tension and torsion, with and without shear, etc.), the force amplitude (e.g., angle or elongation), the frequency and duration of the application, and the duration of the periods of stimulation and rest.

The method for producing the specific tissue type ex vivo is an adaptation of the above described method for producing an ACL. Components involved include pluripotent cells, a three-dimensional matrix to which cells can adhere, and a plurality of anchors which have a face suitable for matrix attachment. The pluripotent cells (preferably bone marrow stromal cells) are seeded in the three dimensional matrix by means to uniformly immobilize the cells within the matrix. The number of cells seeded is also not viewed as limiting, however, seeding the matrix with a high density of cells may accelerate tissue generation.

The specific forces applied are to be determined for each tissue type produced through examination of native tissue and the mechanical stimuli experienced in vivo. A given tissue type experiences characteristic forces which are dictated by location and function of the tissue within the body. For instance, cartilage is known to experience a combination of shear and compression/tension in vivo, bone experiences compression. Determination of the specific mechanical stimuli experienced in vivo by a given tissue is within the means of one of skill in the art.

Additional stimuli (e.g., chemical stimuli, electromagnetic stimuli) can also be incorporated into the above described methods for producing bioengineered ligaments, tendons and other tissues. Cell differentiation is known to be influenced by chemical stimuli from the environment, often produced by surrounding cells, such as secreted growth or differentiation factors, cell-cell contact, chemical gradients, and specific pH levels, to name a few. Other more unique stimuli are experienced by more specialized types of tissues (e.g., the electrical stimulation of cardiac muscle). The application of such tissue specific stimuli (e.g., 1–10 ng/ml transforming growth factor beta-1 (TGF-$\beta$1) independently or in concert with the appropriate mechanical forces is expected to facilitate differentiation of the cells into a tissue which more closely approximates the specific natural tissue.

Tissues produced by the above described methods provide an unlimited pool of tissue equivalents for surgical implantation into a compatible recipient, particularly for replacement or repair of damaged tissue. Engineered tissues may also be utilized for in vitro studies of normal or pathological tissue function, e.g., for in vitro testing of cell- and tissue-level responses to molecular, mechanical, or genetic manipulations. For example, tissues based on normal or transfected cells can be used to assess tissue responses to biochemical or mechanical stimuli, identify the functions of specific genes or gene products that can be either over-expressed or knocked-out, or to study the effects of pharmacological agents. Such studies will likely provide more insight into ligament, tendon and tissue development, normal and pathological function, and eventually lead toward fully functional tissue engineered replacements, based in part on already established tissue engineering approaches, new insights into cell differentiation and tissue development, and the use of mechanical regulatory signals in conjunction with cell-derived and exogenous biochemical factors to improve structural and functional tissue properties.

The production of engineered tissues such as ligaments and tendons also has the potential for applications such as harvesting bone marrow stomal cells from individuals at high risk for tissue injury (e.g., ACL rupture) prior to injury. These cells could be either stored until needed or seeded into the appropriate matrix and cultured and differentiated in vitro under mechanical stimuli to produce a variety of bioengineered prosthetic tissues to be held in reserve until needed by the donor. The use of bioengineered living tissue prosthetics that better match the biological environment in vivo, provide the required physiological loading to sustain for example, the dynamic equilibrium of a normal, fully functional ligament, should reduce rehabilitation time for a recipient of a prosthesis from months to weeks, particularly if the tissue is pre-grown and stored. Benefits include a more rapid regain of functional activity, shorter hospital stays, and fewer problems with tissue rejections and failures.

It is to be understood that the present invention is not intended to be limited to a silk-fiber-based matrix for producing ACL, and other ligaments and tendons, as well as other tissues, such as cartilage, bone, skin and blood vessels are contemplated by the present invention by utilizing the novel silk-fiber based matrix seeded with the appropriate cells and exposed to the appropriate mechanical stimulation if necessary, for proliferating and differentiating into the desired ligament, tendon or tissue.

Additionally, the present invention is not limited to using bone marrow stromal cells for seeding on the matrix, and other progenitor, pluripotent and stem cells, such as those in bone, muscle and skin for example, may also be used to differentiate into ligaments and other tissues.

The invention is further defined by reference to the following examples. It will be apparent to those skilled in the art that many modifications, both to the materials and methods, may be practiced without departing from the purpose and interest of the invention.

EXAMPLES

Example 1 a. Preparation of Silk Films

Raw *Bombyx mori* silkworm fibers, shown in FIG. 1A, were extracted to remove sericin, the glue-like protein coating the native silk fibroin (see FIGS. 1A–C). The appropriate number of fibers per group were arranged in parallel and extracted in an aqueous solution of 0.02M $Na_2CO_3$ and 0.3% (w/v) Ivory soap solution for 60 min at 90° C., then rinsed thoroughly with water to extract the glue-like sericin proteins.

b. Preparation of and Properties of the Silk-Fiber Based Matrix Construct

Costello's equation for a three-strand wire rope was derived to predict mechanical properties of the silk-fiber-based matrix. The derived model is a series of equations that when combined, take into account extracted silk fiber material properties and desired matrix geometrical hierarchy to compute the overall strength and stiffness of the matrix as a function of pitch angle for a given level of geometrical hierarchy The material properties of a single silk fiber include fiber diameter, modulus of elasticity, Poisson's ratio, and the ultimate tensile strength (UTS). Geometrical hierarchy may be defined as the number of twisting levels in a given matrix level. Each level (e.g., group, bundle, strand, cord, ligament) is further defined by the number of groups of fibers twisted about each other and the number of fibers in each group of the first level twisted where the first level is define as a group, the second level as a bundle, the third as a strand and the fourth as a cord, the fifth as the ligament).

The model assumes that each group of multiple fibers act as a single fiber with an effective radius determined by the number of individual fibers and their inherent radius, i.e., the model discounts friction between the individual fibers due to its limited role in given a relatively high pitch angle.

Two applicable geometries (Matrix 1 and Matrix 2) of the many matrix geometrical configurations (see Table 2, supra) computed to yield mechanical properties mimicking those of a native ACL were derived for more detailed analysis. A six-cord construct was selected for use as the ACL replacement. Matrix configurations are as follows: Matrix 1: 1 ACL prosthesis=6 parallel cords; 1 cord=3 twisted strands (3 twists/cm); 1 strand=6 twisted bundles (3 twists/cm); 1 bundle=30 parallel washed fibers; and Matrix 2: 1 ACL matrix=6 parallel cords; 1 cord=3 twisted strands (2 twists/cm); 1 strand=3 twisted bundles (2.5 twists/cm); 1 bundle=3 groups (3 twists/cm); 1 group=15 parallel extracted silk fibroin fibers. The number of fibers and geometries were selected such that the silk prostheses are similar to the ACL biomechanical properties in UTS, linear stiffness, yield point and % elongation at break (see Table 2, supra), thus serving as a solid starting point for the development of a tissue engineered ACL.

Figure 1D:
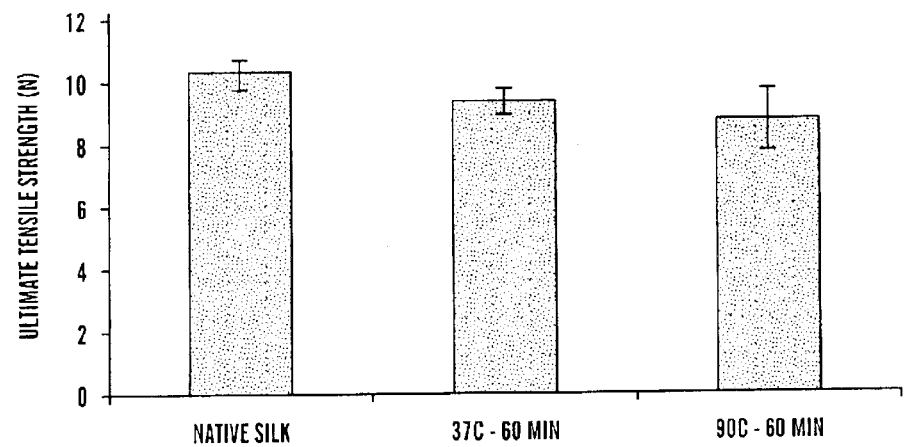
FIG. 1D is a chart showing ultimate tensile strength (UTS) as a function of extraction conditions.

Mechanical properties of the silk fibroin were characterized using a servohydralic Instron 8511 tension/compression system with Fast-Track software (see FIG. 1D). Single pull-to-failure and fatigue analysis were performed on single silk fibers, extracted fibroin and organized cords. Fibers and fibroin were organized in both parallel and wire-rope geometries (Matrix 1 (see FIG. 2A) and Matrix 2 (see FIG. 2B)) for characterization. Single pull to failure testing was performed at a strain rate of 100%/sec; force elongation histograms were generated and data analyzed using Instron Series IX software. Both Matrix 1 and Matrix 2 yielded similar mechanical and fatigue properties to the ACL in UTS, linear stiffness, yield point and % elongation at break (see Table 2 and FIG. 3).

Figure 3A:
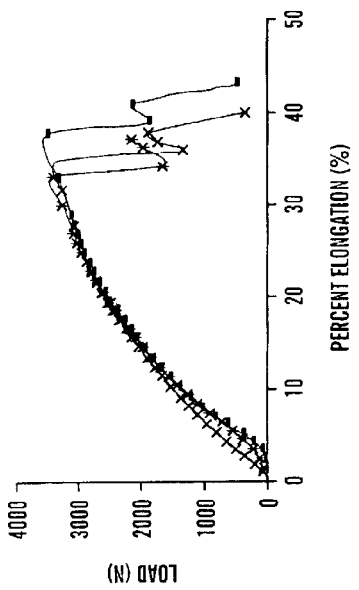
FIG. 3A illustrates load-elongation curves (N=5) for Matrix 1 formed from six parallel silk fibroin cords illustrated in FIG. 2A.
Figure 3B:
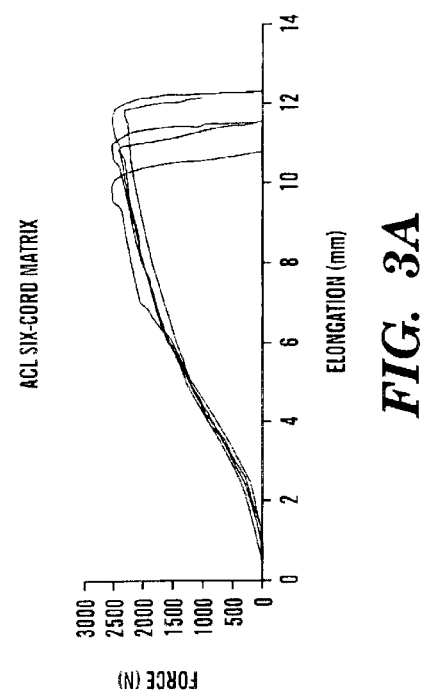
FIG. 3B is a chart of cycles to failure at UTS, 1680 N, and 1200 N loads (n=5 for each load) illustrating Matrix 1 fatigue data. Regression analysis of Matrix 1 fatigue data, when extrapolated to physiological load levels (400 N) to predicite number of cycles to failure in vivo, indicates a matrix life of 3.3 million cycles.
Figure 3C:
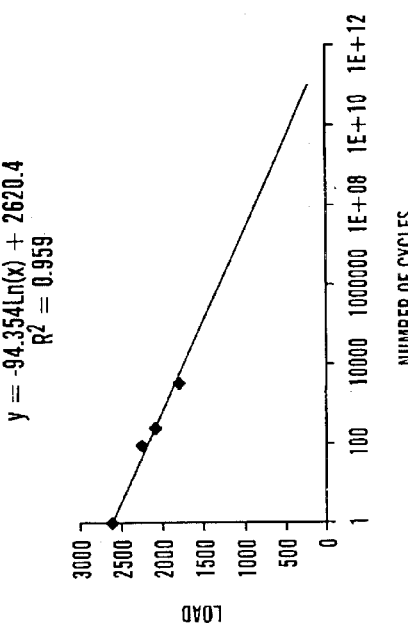
FIG. 3C illustrates load-elongation curves for Matrix 2 (N=3) formed from six parallel silk fibroin cords as illustrated in FIG. 2B.
Figure 3D:
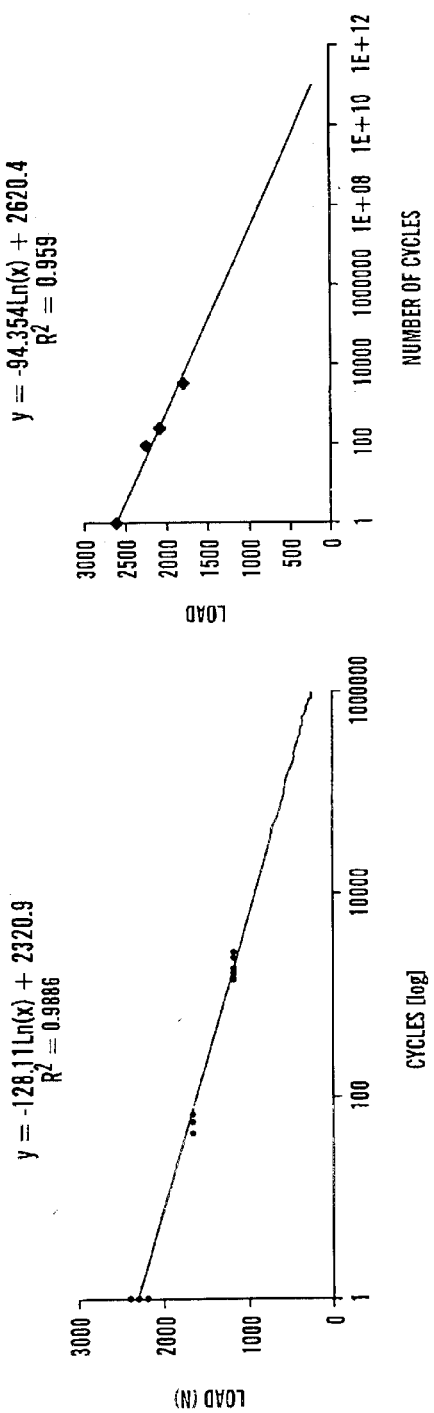
FIG. 3D is a chart of cycles to failure at UTS, 2280N, 2100N and 1800N loads (N=3 for each load) illustrating Matrix 2 fatigue data. Regression analysis of Matrix 2 fatigue data, when extrapolated to physiological load levels (400 N) to predicite number of cycles to failure in vivo, indicates a matrix life of greater than 10 million cycles.

Fatigue analyses were performed using a servohydraulic Instron 8511 tension/compression system with Wavemaker software on single cords of both Matrix 1 and Matrix 2. Data was extrapolated to represent the 6-cord ACL prostheses, which is shown in FIGS. 3B and 3D. Cord ends were embedded in an epoxy mold to generate a 3 cm long construct between anchors. Cycles to failure at UTS, 1,680N and 1,200N (N=5 for each load) for Matrix 1 (see FIG. 3B) and at UTS, 2280N, 2100N and 1800N loads (n=3 for each load) for Matrix 2 (see FIG. 3D) were determined using a H-sine wave function at 1 Hz generated by Wavemaker 32 version 6.6 (Instron, Canton, Mass.). Fatigue testing was conducted in a neutral phosphate buffered saline (PBS) solution at room temperature.

Results

Complete sericin removal was observed after 60 min at 90° C. as determined by SEM (see FIGS. 1A–C). Removal of sericin from silk fibers altered the ultrastructure of the fibers, resulting in a smoother fiber surface and the underlying silk fibroin was revealed (shown in FIGS. 1A–C), with average diameter ranging between 20–40 $\mu$m. The fibroin exhibited a significant 15.2% decrease in ultimate tensile strength (1.033+/-0.042 N/fiber to 0.876+/-0.1N/fiber) ($p<0.05$, paired Students t-test) (see FIG. 1D). The mechanical properties of the optimized silk matrices (see FIG. 2) are summarized in Table 1 above and in FIG. 3A (for Matrix 1) and in FIG. 3C (for Matrix 2). It is evident from these results that the optimized silk matrices exhibited values comparable to those of native ACL, which have been reported to have an average ultimate tensile strength (UTS) of ~2100N, stiffness of ~250N/nm, yield point ~2100N and 33% elongation at break (See Woo, SL-Y, et al., The Tensile Properties of Human Anterior Cruciate Ligament (ACL) and ACL Graft Tissue in Knee Ligaments: Structure, Function, Injury and Repair, An exemplary anchor system is disclosed in applicant's co-pending application U.S. Ser. No. 09/950,561, filed Sept. 10, 2001 and currently pending. The matrix is attached to the anchors via contact with the anchor face or alternatively by actual penetration of the matrix material through the anchor material. Because the force applied to the matrix via the anchors dictates the final ligament produced, the size of the final ligament produced is, in part, dictated by the size of the attachment site of the anchor. One of skill in the art will apprreciate that an anchor of appropriate size to the desired final ligament should be used. A preferred anchor shape for the formation of an ACL is a cylinder. However, one of skill in the art will appreciate that other anchor shapes and sizes will also function adequately. In a preferred embodiment, anchors have an appropriate size and composition for direct insertion into bone tunnels in the femur and tibia of a recipient of the bioengineered ligament.

Example 2

Cell Isolation and Culture

Bone Marrow Stromal Cells (BMSC), pluripotent cells capable of differentiating into osteogenic, chondrogenic, tendonogenic, adipogenic and myogenic lineages, were chosen since the formation of the appropriate conditions can direct their differentiation into the desired ligament fibroblast cell line (Markolf et al., *J. Bone Joint Surg.* 71A: 887–893 (1989); Caplan et al., Mesenchymal stem cells and tissue repair. In *The Anterior Cruciate Ligament: Current and Future Concepts*, Ed. D. W. Jackson et al., Raven Press, Ltd, New York (1993); Young et al.,*J. Orthopaedic Res.* 16: 406–413 (1998)).

Human BMSCs were isolated from bone marrow from the iliac crest of consenting donors $\leq 25$ years of age by a commercial vendor (Cambrex, Walkersville, Md.). Twenty-two milliliters of human marrow was aseptically aspirated into a 25 ml syringe containing three milliliters of heparinized (1000 units per milliliter) saline is solution. The heparinized marrow solution was shipped overnight on ice to the laboratory for bone marrow stromal cells isolation and culture. Upon arrival from the vendor, the twenty-five milliliter aspirates were resuspended in Dulbecco's Modified Eagle Medium (DMEM) supplemented with 10% fetal bovine serum (FBS), 0.1 mM nonessential amino acids, 100 U/ml penicillin, 100 mg/L streptomycin (P/S), and 1 ng/ml basic fibroblast growth factor (bFGF) (Life Technologies, Rockville, Md.) and plated at 8–10 microliters of aspirate/$cm^2$ in tissue culture flasks. Fresh medium was added to the marrow apirates twice a week for up to nine days of culture. BMSCs were selected based on their ability to adhere to the tissue culture plastic; non-adherent hematopoietic cells were removed during medium replacement after 9–12 days in culture. Medium was changed twice per week thereafter. When primary BMSC became near confluent (12–14 days), they were detached using 0.25% trypsin/1 mM EDTA and replated at $5 \times 10^3$ cells/$cm^2$. First passage (P1) hBMSCs were trypsinized and frozen in 8% DMSO/10% FBS/DMEM for future use.

Silk Matrix Cell Seeding

Frozen P1 hBMSCs were defrosted, replated at $5 \times 10^3$ cells/$cm^2$ (P2), trypsinized when near confluency, and used for matrix seeding. Sterilized (ethylene oxide) silk matrices (specifically single cords of Matrix 1&2, bundles of 30 parallel extracted silk fibers and wire-ropes of collage fibers) were seeded with cells in customized seeding chambers (1 ml total volume) machined in Teflon blocks to minimize cell-medium volume and increase cell-matrix contact. Seeded matrices, following a 4 hour incubation period with the cell slurry ($3.3 \times 10^6$ BMSCs/ml) were transferred into a petri dish contain an appropriate amount of cell culture medium for the duration of the experiments.

To determine the degradation rate of the silk fibroin, ultimate tensile strength (UTS) was measured as a function of cultivation period in physiological growth conditions, i.e., in cell culture medium. Groups of 30 parallel silk fibers 3 cm in length were extracted, seeded with hBMSCs, and cultured on the fibroin over 21 days at 37° C. and 5% $CO_2$. Non-seeded control groups were cultured in parallel. Silk fibroin UTS was determined as a function of culture duration for seeded and non-seeded groups.

Results

Figure 4A:
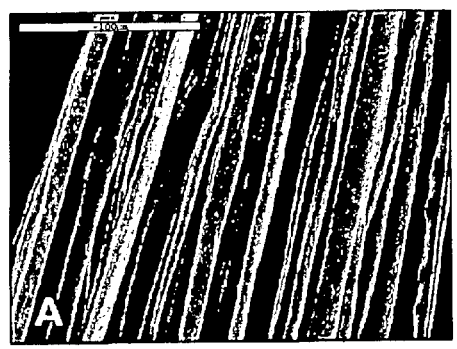
FIG. 4A illustrates SEM of extracted silk fibroin prior to seeding with cells.
Figure 4B:
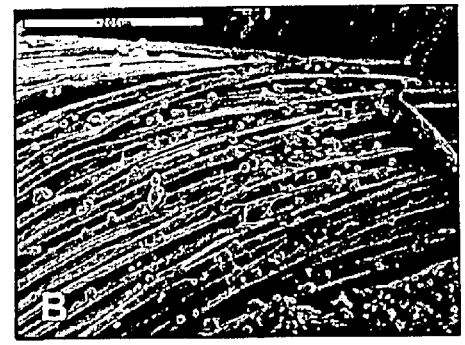
FIG. 4B illustrates SEM of bone marrow stromal cells seeded and attached on silk fibroin immediately post seeding.
Figure 4C:
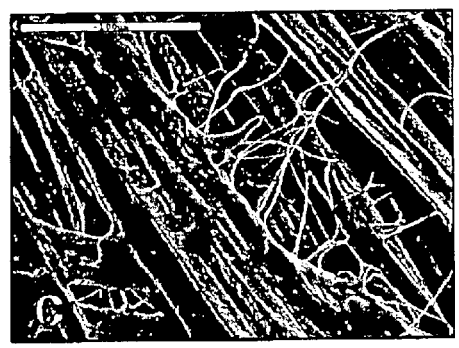
FIG. 4C illustrates SEM of bone marrow cells attached and spread on silk fibroin 1 day post seeding.
Figure 4D:
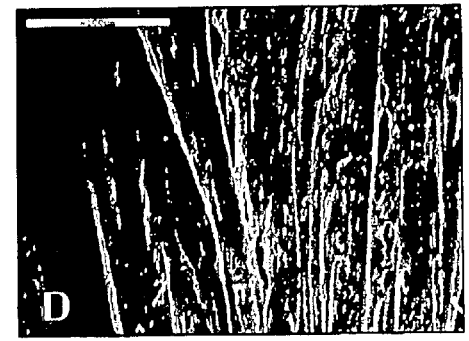
FIG. 4D illustrates SEM of bone marrow stromal cells seeded on silk fibroin 14 days post seeding forming an intact cell-extracellular matrix sheet.
Figure 5A:
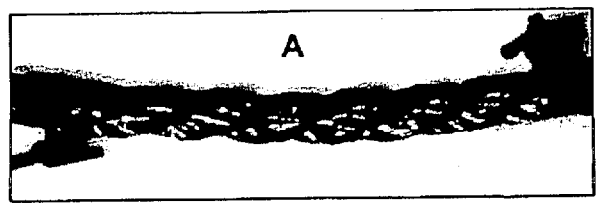
FIG. 5A illustrates a 3 cm length of the silk fibroin cord illustrated in FIG. 2A and seeded with bone marrow stromal cells, cultured for 14 days in a static environment and stained with MTT to show even cell coverage of the matrix following the growth period.
Figure 5B:
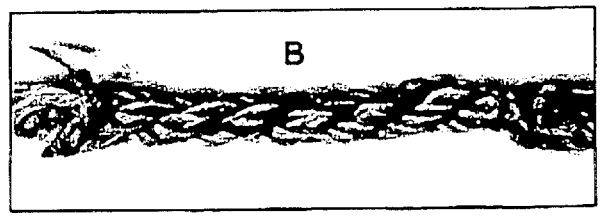
FIG. 5B illustrates a control strand of silk fibroin cord 3 cm in length stained with MTT.
Figures 10A, 10B, 10C:
FIG. 10 illustrates bone marrow stromal cells seeded and grown on collagen fibers for (A) 1 day and (B) 21 days; (C) RT-PCR and gel electrophoretic analysis of collagen I and III expression vs. the housekeeping gene GAPDH: a=Collagen I, day 14; b=Collagen I, day 18; c=Collagen III, day 14; d=Collagen III, day 18; e=GAPDH, day 14; f=GAPDH, day 18. Collagen type II (as a marker for cartilage) and bone sialoprotein (as a marker of bone tissue formation) were not detected indicating a ligament specific differentiation response.

The response of bone marrow stromal cells to the silk matrix was also examined. BMSCs readily attached and grew on the silk and collagen matrices after 1 day in culture (See FIGS. 4A–C and FIG. 10A), and formed cellular extensions to bridge neighboring fibers. As shown in FIG. 4D and FIG. 10B, a uniform cells sheet covering the construct was observed at 14 and 21 days of culture, respectively. MTT analysis confirmed complete matrix coverage by seeded BMSCs after 14 days in culture (see FIG. 5). Total DNA quantification of cells grown on Matrix 1 (see FIG. 6A) and Matrix 2 (see FIG. 6B) confirmed that BMSCs proliferated and grew on the silk construct with the highest amount of DNA measured after 21 and 14 days, respectively, in culture.

Figure 7:
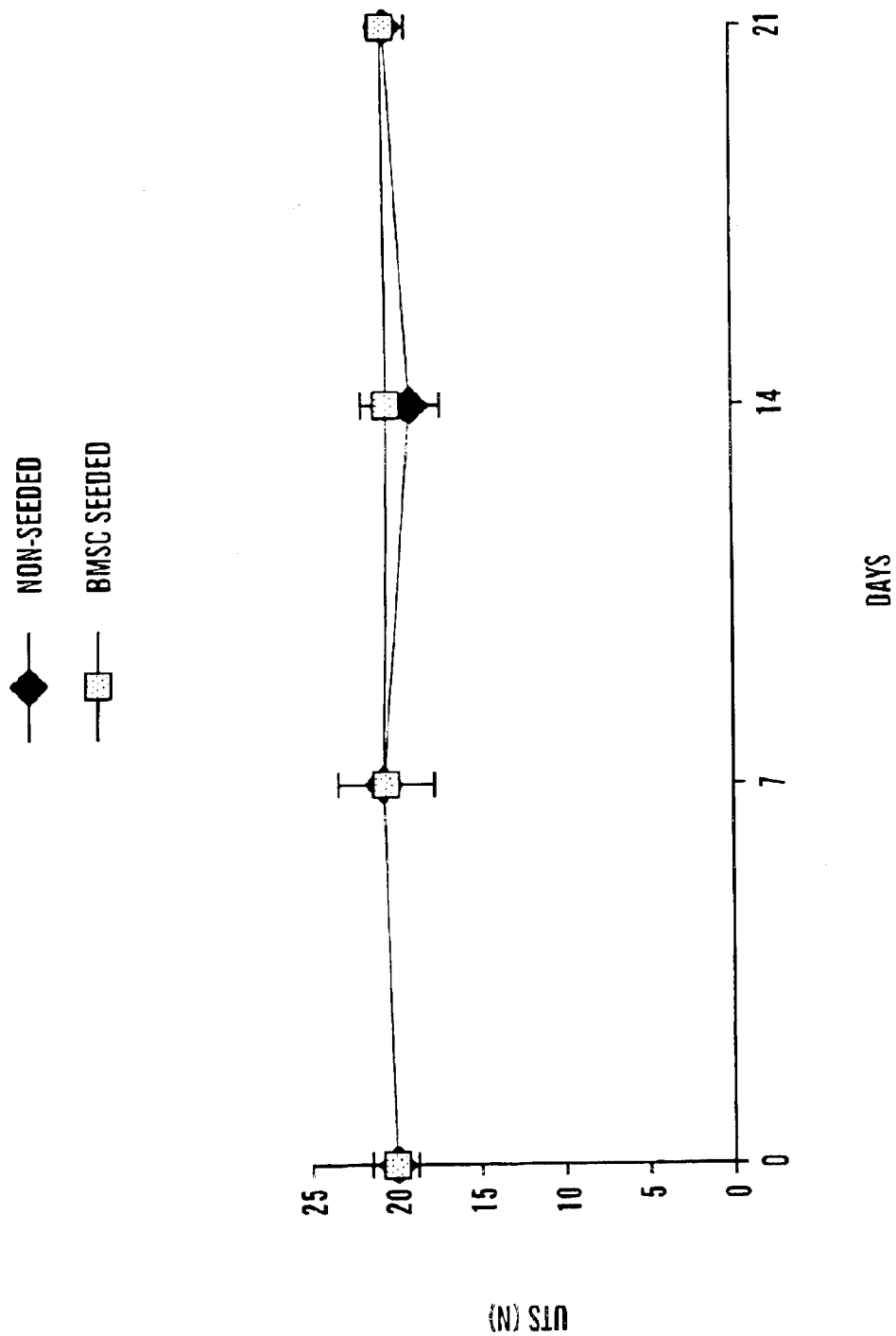
FIG. 7 illustrates the ultimate tensile strength of a 30 silk fiber extracted construct which is either seeded with bone marrow stromal cells or non-seeded over 21 days of culture in physiological growth conditions.

Both BMSC seeded or non-seeded extracted control silk fibroin groups of 30 fibers, maintained their mechanical integrity as a function of culture period over 21 days (see FIG. 7).

Figure 8:
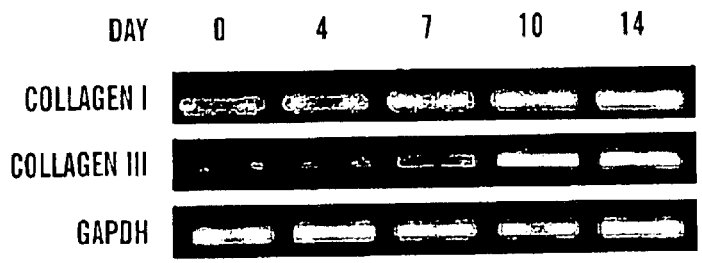
FIG. 8 illustrates gel eletrophoretic analysis of RT-PCR amplification of selected markers over time. The gel shows upregulation in both collagen types I and III expression levels normalized to the housekeeping gene, GAPDH by bone marrow stromal cell grown on Matrix 2 over 14 days in culture. Collagen type II (as a marker for cartilage) and bone sialoprotein (as a marker of bone tissue formation) were not detected indicating a ligament specific differentiation response by the BMSCs when cultured with Matrix 2.
Figure 9A:
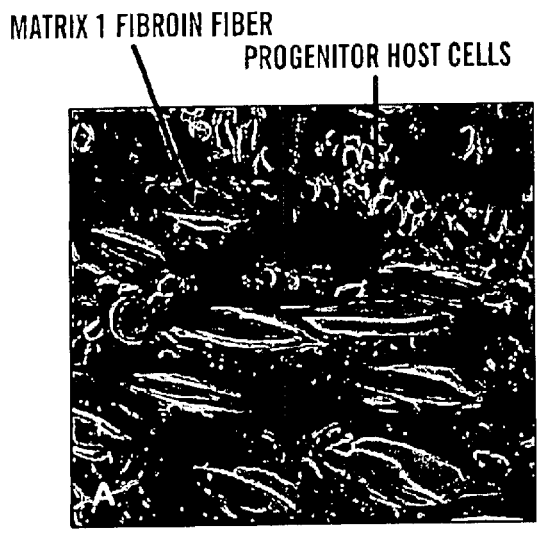
FIG. 9 illustrates a single cord of Matrix 1 (not seeded at the time of implantation) following six weeks of implantation in vivo and used to reconstruct the medial collateral ligament (MCL) in a rabbit model. (A) shows Matrix 1 fibroin fibers surrounded by progenitor host cells and tissue ingrowth into the matrix and around the individual fibroin fibers visualized by hematoxylin and eosin staining; (B) shows collagenous tissue ingrowth into the matrix and around the individual fibroin fibers visualized by trichrome staining.
Figure 9B:
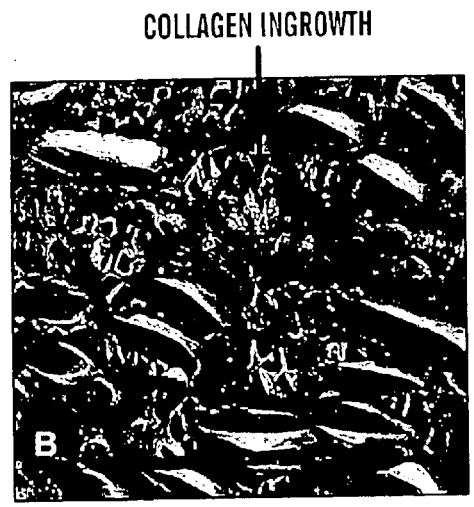
Figure 11:
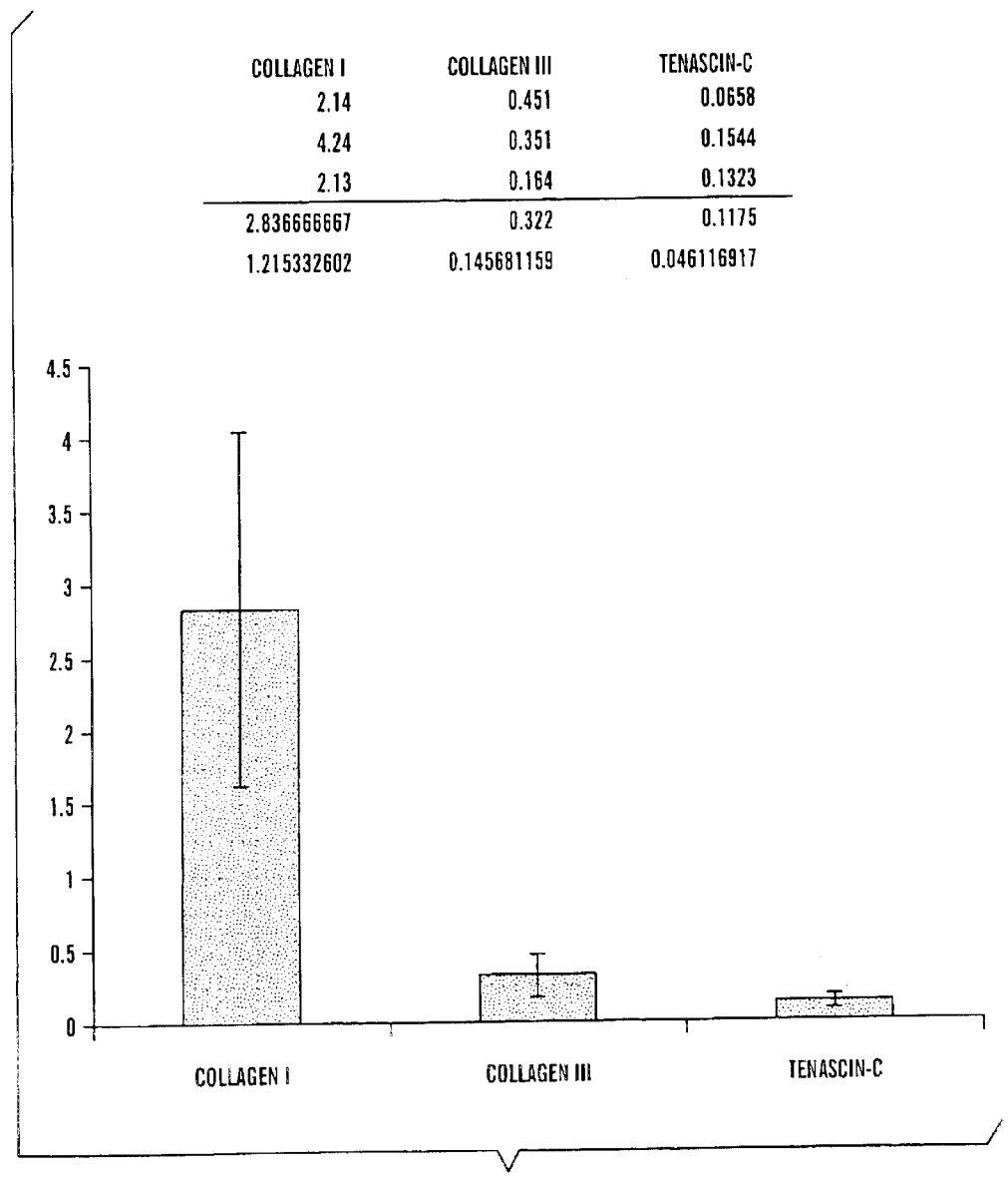
FIG. 11 illustrates real-time quantitative RT-PCR at 14 days which yielded a transcript ratio of collagen I to collagen III, normalized to GAPDH, of 8.9:1.

RT-PCR analysis of BMSCs seeded on cords of Matrix 2 indicated that both collagen I & III were upregulated over 14 days in culture (FIG. 8). Collagen type II and bone sialoprotein (as indicators of cartilage and bone specific differentiation, respectively) were either not detectable or negligibly expressed over the cultivation period. Real-time quantitative RT-PCR at 14 days yielded a transcript ratio of collagen I to collagen III, normalized to GAPDH, of 8.9:1 (see FIG. 11). The high ratio of collagen I to collagen III indicates that the response is not wound healing or scar tissue formation (as is observed with high levels of collagen type III), but rather ligament specific; the relative ratio of collagen I to collagen III in a native ACL is ~6.6:1 (Amiel et al., In *Knee Ligaments: Structure, Function, Injury, and Repair*. 1990).

Example 3

Studies are conducted to provide insight into the influence of directed multi-dimensional mechanical stimulation on ligament formation from bone marrow stromal cells in the bioreactor system. The bioreactor is capable of applying independent but concurrent cyclic multi-dimensional strains (e.g., translation, rotation) to the developing ligaments. After a 7 to 14 day static rest period (time post seeding), the rotational and translation strain rates and linear and rotational deformation are kept constant for 1 to 4 weeks. Translational strain (3.3%–10%, 1–3 mm) and rotational strain (25%, 90°) are concurrently applied at a frequency of 0.0167 Hz (one full cycle of stress and relaxation per minute) to the silk-based matrices seeded with BMSCs; an otherwise identical set of bioreactors with seeded matrices without mechanical loading serve as controls. The ligaments are exposed to the constant cyclic strains for the duration of the experiment days.

Following the culture period, ligament samples, both the mechanically challenged as well as the controls (static) are characterized for: (1) general histomorphological appearance (by visual inspection); (2) cell distribution (image processing of histological and MTT stained sections); (3) cell morphology and orientation (histological analysis); and (4) the production of tissue specific markers (RT-PCR, immunostaining).

Mechanical stimulation markedly affects the morphology and organization of the BMSCs and newly developed extracellular matrix, the distribution of cells along the matrix, and the upregulation of a ligament-specific differentiation cascade; BMSCs align along the long axis of the fiber, take on a spheroid morphology similar to ligament/tendon fibroblasts and upregulate ligament/tendon specific markers. Newly formed extracellular matrix is expected to align along the lines of load as well as the long axis of the matrix. Directed mechanical stimulation is expected to enhance ligament development and formation in vitro in a bioreactor resulting from BMSCs seeded on the novel silk-based matrix. The longitudinal orientation of cells and newly formed matrix is similar to ligament fibroblasts found within an ACL in vivo (Woods et al. *Amer. J. Sports Med.* 19: 48–55 (1991)). Furthermore, mechanical stimulation maintains the correct expression ratio between collagen I transcripts and collagen type III transcripts (e.g., >7:1) indicating the presence of newly formed ligament tissue versus scare tissue formation. The above results will indicate that the mechanical apparatus and bioreactor system provide a suitable environment (e.g., multi-dimensional strains) for in vitro formation of tissue engineered ligaments starting from bone marrow stromal cells and the novel silk-based matrix.

The culture conditions used in these preliminary experiments can be further expanded to more accurately reflect the physiological environment of a ligament (e.g. increasing the different types of mechanical forces) for the in vitro creation of functional equivalents of native ACL for potential clinical use. These methods are not limited to the generation of a bioengineered ACL. By applying the appropriate magnitude and variety of forces experienced in vivo, any type of ligament in the body can be produced ex vivo by the methods of the present invention.

We claim:

1. A silk-fiber-based matrix composition comprising sericin-extracted silkworm fibroin fibers, said fibers being biocompatible and helically organized into fiber bundles, wherein said matrix supports ingrowth of cells around said fibroin fibers and is biodegradable.

2. The matrix as recited in claim 1, wherein the silk-fiber based matrix comprises fibroin fibers obtained from *Bombyx mori* silkworm.

3. The matrix as recited in claim 1, wherein the matrix comprises a composite of the sericin-extracted fibroin fibers and collagen fibers.

4. The matrix as recited in claim 1, wherein the matrix comprises a composite of the sericin-extracted fibroin fibers and one or more silk foams, films, meshes or sponges.

5. The matrix as recited in claim 1, wherein the matrix comprises a composite of the sericin-extracted fibroin fibers and one or more degradable polymers selected from group consisting of Collagens, Polylactic acid or its copolymers, Polyglycolic acid or its copolymers, Polyanhydrides, Elastin, Glycosamino glycans, and Polysaccharides.

6. The matrix as recited in claim 1, further comprising pluripotent or fibroblast cells seeded on said matrix.

7. The matrix as recited in claim 6, wherein said pluripotent or fibroblast cells are autologous.

8. The matrix as recited in claim 7, wherein said pluripotent or fibroblast cells are allogeneic.

9. The matrix as recited in claim 7, wherein said pluripotent cells are selected from the group consisting of bone marrow stromal cells and adult or embryonic stem cells.

10. The matrix as recited in claim 7, wherein said fibroblast cells are mature human ACL fibroblast cells.

11. The matrix as recited in claim 7, wherein said pluripotent or fibroblast cells proliferate and differentiate on said matrix to form said predetermined ligament or tendon.

12. The matrix as recited in claim 7, further comprising a surface modification agent which enhances proliferation and differentiation of said pluripotent or fibroblast cells on said matrix.

13. The matrix as recited in claim 1, wherein said matrix comprises a shape of a ligament or tendon selected from the group consisting of anterior cruciate ligament, posterior cruciate ligament, rotator cuff tendon, medial collateral ligament of the elbow, flexor tendon of the hand, ligaments and tendons of the temporomandibular joint, and lateral ligament of the ankle.

14. The matrix as recited in claim 13, wherein said ligament is an anterior cruciate ligament.

15. The matrix of claim 1, wherein said helically-organized fibers comprise a cylindrical shape.

16. The matrix of claim 12, wherein said surface modification comprises an arginine-glycine-aspartate peptide.

17. The matrix of claim 1, wherein said matrix comprises an ultimate tensile strength of greater than 2000N and a linear stiffness of between 100–600N/mm.

18. A silk-fiber-based matrix comprising helically organized fiber bundles of sericin-extracted biodegradable silkworm fibroin fibers and bone marrow stromal cells attached thereto.

19. A composition consisting essentially of sericin-extracted silkworm fibroin fibers, said fibers being biodegradable and organized into a matrix being helically organized into fiber bundles and comprising an ultimate tensile strength of greater than 2000N and a linear stiffness of between 100–600N/mm, wherein sericin is completely removed from said fiber.

* * * * *